(12) United States Patent
Yuan et al.

(10) Patent No.: US 8,019,092 B2
(45) Date of Patent: Sep. 13, 2011

(54) AURAL DEVICE WITH WHITE NOISE GENERATOR

(75) Inventors: Yi-Cheng Yuan, Keelung (TW); Ching-Sheng Yu, Taipei (TW); Stuart Cochrane, Palm Springs, CA (US)

(73) Assignee: Savannah Marketing Group Inc., Palm Springs, CA (US)

( * ) Notice: Subject to any disclaimer, the term of this patent is extended or adjusted under 35 U.S.C. 154(b) by 178 days.

(21) Appl. No.: 12/606,879

(22) Filed: Oct. 27, 2009

(65) Prior Publication Data

US 2011/0096938 A1   Apr. 28, 2011

(51) Int. Cl.
*H04R 3/02* (2006.01)
*H04R 25/00* (2006.01)

(52) U.S. Cl. ...................... 381/73.1; 381/381

(58) Field of Classification Search .................. 381/73.1, 381/74, 309, 330, 327, 381
See application file for complete search history.

(56) References Cited

U.S. PATENT DOCUMENTS

| 4,727,582 | A | * | 2/1988 | de Vries et al. ............... 381/330 |
|---|---|---|---|---|
| 4,777,937 | A | | 10/1988 | Rush |
| 4,821,247 | A | | 4/1989 | Grooms |
| 5,167,236 | A | | 12/1992 | Junker |
| 5,313,678 | A | | 5/1994 | Redewell |
| 5,606,621 | A | | 2/1997 | Reiter et al. |
| 5,881,390 | A | | 3/1999 | Young |
| 6,014,345 | A | | 1/2000 | Schmadeka |
| 6,267,721 | B1 | | 7/2001 | Welles |
| 6,906,983 | B2 | | 6/2005 | Williams |
| 7,039,208 | B2 | | 5/2006 | Wagner et al. |
| 7,054,957 | B2 | | 5/2006 | Armitage |
| 7,062,057 | B2 | | 6/2006 | Wu |
| 7,206,429 | B1 | | 4/2007 | Vossler |
| 7,248,705 | B1 | | 7/2007 | Mishan |
| 7,262,992 | B2 | | 8/2007 | Shibata et al. |
| 7,480,388 | B1 | | 1/2009 | Crook |
| 2003/0235313 | A1 | | 12/2003 | Kurzweil |
| 2004/0136555 | A1 | | 7/2004 | Enzmann |
| 2006/0020161 | A1 | | 1/2006 | Mageras et al. |
| 2007/0110253 | A1 | | 5/2007 | Anderson et al. |
| 2007/0269065 | A1 | | 11/2007 | Kilsgaard |

OTHER PUBLICATIONS http://www.inearmatters.net, A Past Review: Multiple IEM Shoot out, Nov. 30, 2008.
http://www.wmexperts.com/reviews/bluetooth_headsets/review_motorola_motorokr_s9_st_1.html, Review: Motorola Motorokr S9 Stereo Bluetooth Headset, Mar. 6, 2008.

* cited by examiner

*Primary Examiner* — Ping Lee
(74) *Attorney, Agent, or Firm* — Jeffrey G. Sheldon; Sheldon Mak & Anderson

(57) ABSTRACT

An aural device to be worn over the ear of a user during sleeping hours which generates white noise.

17 Claims, 8 Drawing Sheets

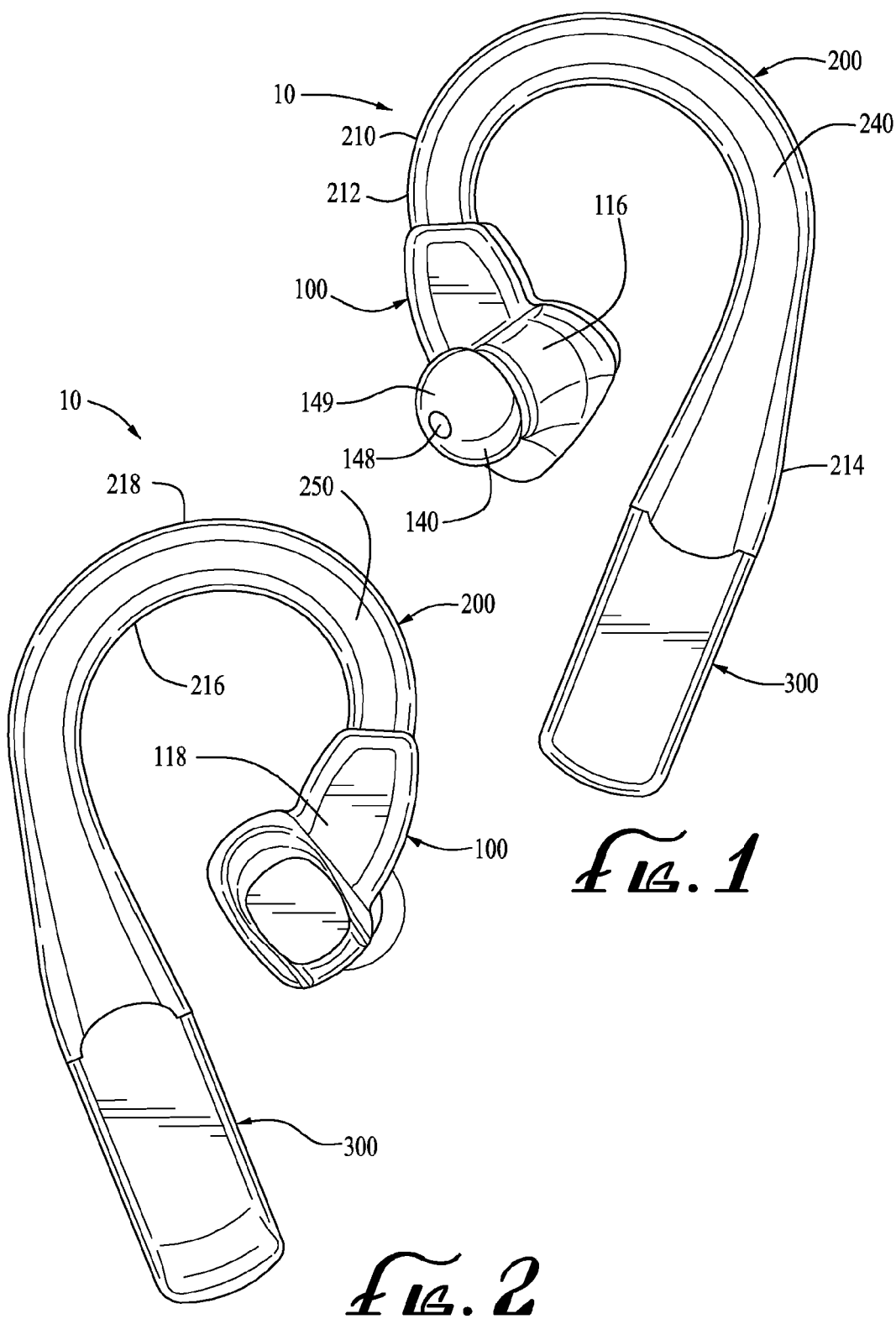

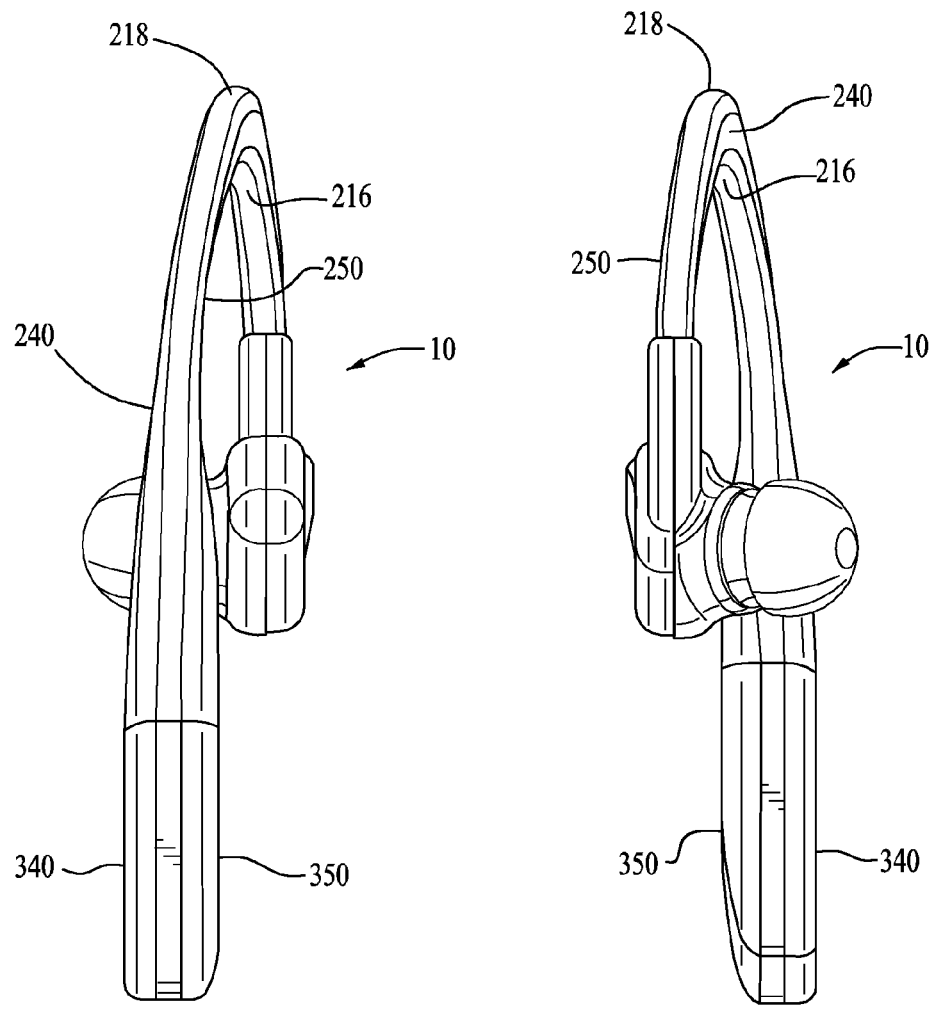
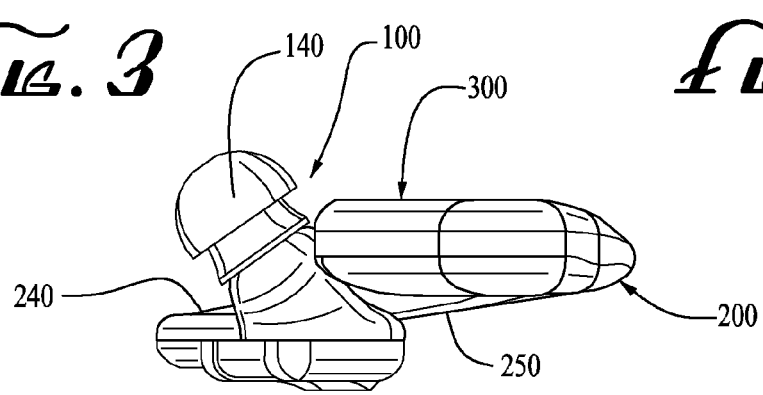

AURAL DEVICE WITH WHITE NOISE GENERATOR

BACKGROUND

Sound conditioners are known which camouflage undesirable noise in the environment by generating white noise or background sounds such as the sound of ocean surf, rain, a rain forest, or a heartbeat. These devices are stand-alone units and usually sit on a night stand or the like for use by individuals at night to aid sleep.

Other mechanisms for avoiding exposure to unwanted sounds include passive mechanisms such as ear plugs or ear covers with noise-absorbing qualities. Active noise cancellation techniques are also known, and involve the use of a microphone for receiving external sounds which are converted into an electrical signal, after which an opposing-phase signal is generated. This opposing-phase signal is then supplied to a speaker in a headset and serves to cancel at least some of the external sounds by destructive interference.

SUMMARY

The present invention comprises an aural device, in particular one for use by a user during sleep, that reduces a user's experience of undesirable environmental noise. The device includes a housing, a structural element projecting away from the housing, and a battery connected to the structural projection. The housing is configured for placement adjacent to the ear canal of a user without covering the pinna and includes a transducer in the interior of the housing; circuitry in electrical communication with the transducer for generating sound; a conduit for conducting sound generated by the transducer from the interior of the housing to the exterior of the housing; and an elastic rim adjacent to the distal end of the conduit for covering the ear canal of a user. Preferably the circuitry of the device includes a white noise generator. In a preferred embodiment, the elastic rim of the housing portion of the device is an eartip and comprises a distal surface which is spherical in shape. The lateral end of the housing also preferably comprises a substantially flat surface for greater user comfort. In addition, the medial end of the housing preferably projects downward with respect to the substantially flat lateral end at an angle of less than 90°.

The projecting structural member is connected at a proximal end to the housing and at a distal end to a battery, and includes an electrical connector which places the battery in electrical communication with circuitry within the housing. The projection further comprises a substantially flat lateral surface and a substantially flat medial surface to provide greater comfort and wearability. In one embodiment, the projection extends from the concha of the ear of a user around the ear and forms an earhook.

The battery of the device is in electrical communication with the circuitry and transducer in the housing through the electrical connector of the projection. The battery is preferably contained in a battery housing having a substantially flat lateral surface and a substantially flat medial surface for greater user comfort. The proximal end of the battery housing in one embodiment is removably securable to the electrical connector, in which case the battery is preferably rechargeable.

The present device can be used in conjunction with a container that not only protects the device when not in use but also allows the battery to be recharged. The container in this embodiment includes both a compartment for enclosing the aural device and a receptacle in the compartment for receiving the proximal end of the battery housing. The receptacle includes an electrical connector that places the battery in electrical communication with a power source. In this embodiment the container further includes circuitry for charging the battery, including LED lights for indicating the charging status of a battery contained in the receptacle.

DRAWINGS

FIG. 1 is a side elevation view of the medial side of an embodiment of the present device.

FIG. 2 is a side elevation view of the lateral side of the device of FIG. 1.

FIG. 3 is a rear side elevation view of the device of FIG. 1.

FIG. 4 is a front side elevation view of the device of FIG. 1.

FIG. 5 is a bottom side elevation view of the device of FIG. 1.

DESCRIPTION

Definitions

Figure 6:
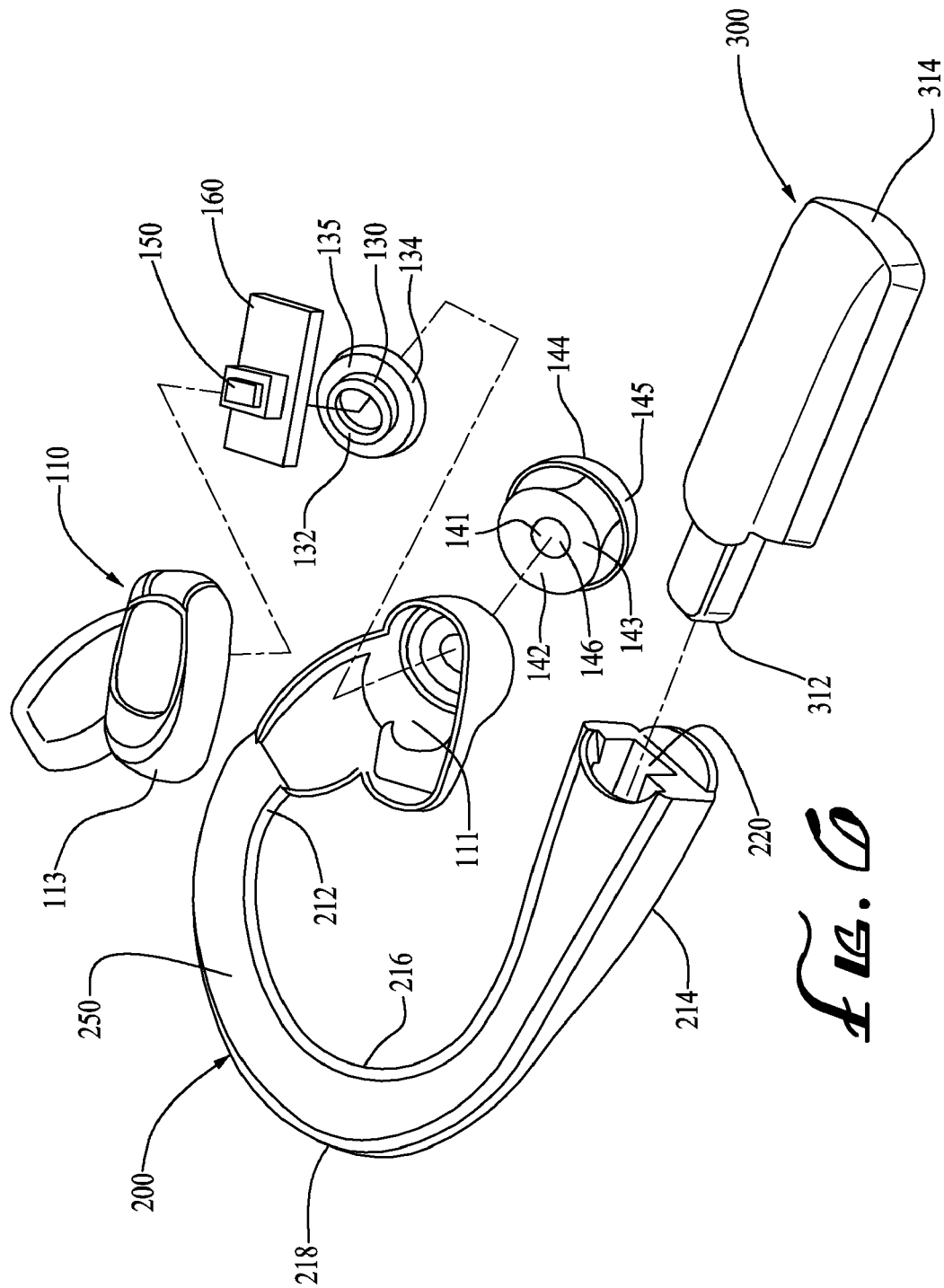
FIG. 6 is an exploded view of the device of FIG. 1.

As used herein, the following terms and variations thereof have the meanings given below, unless a different meaning is clearly intended by the context in which such term is used.

"Concha" refers to the concave portion of the pinna adjacent to the ear canal.

"Coronal plane" refers to a plane which passes through the longitudinal axis of the body which divides the body into dorsal (back) and ventral (front) sections.

"Earhook" refers to a structural element connecting the earpiece of the present device with a battery having a curved shape and extending around the pinna of a user's ear between the skull and the medial side of the pinna. An earhook extends between a ventral portion of the pinna and a dorsal portion when worn by a user.

"Earpiece" refers to a portion of the present device that houses an electro-acoustic transducer for converting electric signals into sounds and that is placed directly outside of the ear canal of a user, without fully covering the pinna of the ear. Typically the earpiece fits within the outer ear bowl (concha) of the ear of a user and covers some or all of the concha.

"Eartip" refers to a structural element attached to the earpiece for conducting sound from the earpiece to the ear of a user and/or for facilitating placement of the earpiece in the outer ear bowl (concha) and/or the ear canal of a user.

"Lateral" refers to a direction or orientation away from the midsaggital plane of a user of the present device.

"Medial" refers to a direction or orientation toward the midsaggital plane of a user of the present device.

A "microcontroller unit" ("MCU") is a device on a single integrated circuit consisting of a relatively simple CPU combined with support functions such as an I/O interface.

"Midsaggital plane" refers to a plane which passes vertically through the midline of the body along its longitudinal axis, dividing the body into left and right halves of approximately equal proportion (with reference to bilateral symmetry).

"Pinna" refers to the externally visible cartilaginous structure of the external ear.

"Transducer" refers to a device for converting an electrical signal into sound waves.

"White noise" refers to a sound or sounds that are random in character, such as sounds derived from a random signal, and in particular to noise signals containing equal power within a fixed bandwidth at any center frequency. White noise can sound like a rushing waterfall or wind blowing through trees. White noise can have different characteristic statistical properties corresponding to different mappings from a source of randomness to the concrete noise. Power distribution in the frequency spectrum is a property which can be used to distinguish different types of white noise. For purposes of the present definition, white noise includes white, pink, blue, and black noise as defined in the Federal Standard 1037C Telecommunications Glossary unless otherwise indicated.

As used herein, the term "comprise" and variations of the term, such as "comprising" and "comprises," are not intended to exclude other additives, components, integers or steps. The terms "a," "an," and "the" and similar referents used herein are to be construed to cover both the singular and the plural unless their usage in context indicates otherwise.

Aural Device

An embodiment of the present device 10 is illustrated in FIGS. 1-6. The device 10 includes an earpiece 100, an earhook 200, and a battery assembly 300. The earpiece 100 includes a housing 110 for a transducer 150 and a microcontroller 160 (shown in FIG. 6). The earhook 200 in this embodiment comprises a projection 210 attached at a proximal end 212 to the earpiece 100 that is shaped to fit over the medial side of the pinna of the ear of a user, i.e. between the user's skull and the medial surface of the pinna, thereby supporting the placement of the earpiece 100 on the ear of a user when worn. The projection 210 attaches to the battery assembly 300 at a distal end 214. in addition to mechanically connecting the earpiece 100 the battery assembly 300, the projection 210 also provides electrical communication between the battery 330 of the battery assembly 300 and the electrical components of the earpiece 100.

Earpiece

The housing 110 of the earpiece 100 of the present device 10 preferably includes both the transducer 150 for generating sound and an MCU 160. These components are contained in an interior portion 111 of the housing 110, which is in communication with a conduit 130. The conduit 130 extends from the interior portion 111 of the housing 110 to the exterior 113 of the housing 110, and is preferably attached or otherwise secured to the housing 110. In some embodiments, the conduit 130 can be integrally formed with the housing 110.

A proximal end 132 of the conduit 130 is positioned adjacent to the outlet of the transducer 150, i.e. the opening the transducer 150 in communication with the diaphragm of the transducer from which sound is emitted. The conduit 130 transmits sounded generated by the transducer 150 from the interior 111 of the housing 110 toward the ear canal of a user when the present device 10 is worn by a user. At a distal end 134 of the conduit 130, the conduit 130 is connected to a rim 145 which is preferably formed from an elastic material, i.e. a material which conforms to the shape of a more rigid material with which it comes into contact, and which is capable of resuming its original shape after stretching or compression. The rim 145 contacts the concha and/or the outer portion of the ear canal of a user when the present device is worn by a user and preferably helps to position the present device 10 in a user's ear. The use of an elastic material for the rim 145 is preferred for applications of the present device designed to mask external sounds, such as during sleep. By conforming to the shape of the portion of the user's ear with which the rim 145 comes into contact, the rim 145 can create a seal around that portion of the ear and thereby help to block the passage of the external sounds into the ear canal of the user.

In the embodiment of the present device 10 shown in the FIGS. 1-6, the rim 145 is part of an eartip 140. The eartip 140 in this embodiment is separately formed from the housing 110 of the earpiece 100, and therefore can be formed from a material which is more pliable and able to conform to the surface of a user's ear. For example, the eartip 140 can be formed from a reversibly deformable (soft) material such as natural or synthetic rubber.

An eartip 140 can be secured to the remainder of the earpiece 100 in a variety of ways known to the art. For example, the eartip 140 can be permanently secured to the earpiece 100 with a chemical adhesive. Preferably, however, when an eartip 140 is used in the present device 10, the eartip 140 is reversibly secured to the remainder of the earpiece 100. In this way, if it is damaged or contaminated in some way, it can be removed from the remainder of the device 10 and replaced.

In the embodiment shown in FIG. 6, the eartip 140 comprises a conduit 141 having a proximal opening 146 at a proximal end 142 which is in communication with the conduit 130 of the earpiece 100 when connected to the earpiece 100. An inwardly projecting circumferential rim or lip 143 at the proximal end 142 is adapted to engage a circumferential rim 135 at the distal end 134 of the conduit 130 in order to reversibly secure the eartip 140 to the remainder of the earpiece 100. In this embodiment the eartip 140 is formed from an elastomeric material and the proximal opening 146 of the eartip conduit 141 has a smaller diameter than the diameter of the rim 135 of the conduit 130, such that the proximal end 142 of the eartip 140 is secured to the conduit 130 by urging the rim 135 of the conduit through the proximal opening 146 of the conduit 141 of the eartip 140. After stretching the material around the proximal opening 146, once the rim 135 is completely through the proximal opening 146, the lip 143 will revert to its previous, smaller diameter and retain the eartip 140 on the housing 110 of the earpiece 100.

The distal end 144 of the eartip 140 is preferably shaped so as to help seal the ear canal of a user when the present device 10 is in use. The distal surface 149 of the distal end 144 of the eartip 140 surrounding the distal opening 148 of the eartip conduit 141 preferably extends outwardly and tapers away from the distal end 144. In one embodiment, the distal surface 149 is spherical in shape and tapers in the manner of a mushroom.

One of the advantages of the present device 10 is that it is configured to be worn comfortably by a user during sleep. Many individuals sleep some or all of the time on their side, in which case the ear (pinna) of the individual contacts a pillow or other surface. In view of this, the lateral surface 118 of the housing 110 preferably does not include projections which might extend beyond the points of contact between a user's ear and the surface on which the ear rests during sleep. More preferably, the lateral surface 118 is substantially flat, with the surface oriented roughly parallel to the user's midsaggital plane (within 30° or less).

The medial surface 116 of the housing 110 is likewise configured for user comfort, and is therefore preferably shaped to conform to the curvature of the outer ear bowl of the ear of a user. The medial surface 116 of the housing 110 therefore preferably projects at an angle with respect to the substantially flat lateral surface 118 of the device 10. Preferably, the angle is less than 90°, and more preferably is between 45° and 60°.

Earhook

The present device 10 also comprises a mechanical projection which extends from the housing 110 to the battery assembly 300 of the present device 10. In the embodiment of the present device shown in FIGS. 1-7, the projection is in the form of an earhook 200, and performs the functions of mechanically connecting the earpiece 100 with the battery assembly 300 and also providing an electrical connection between the electrical components of the present device 10 and the battery assembly 300. As shown in FIGS. 1-6, the earhook 200 is connected at a proximal end 212 to the housing 110 of the earpiece 100 and at a distal end 214 to the battery assembly 300.

Figure 7:
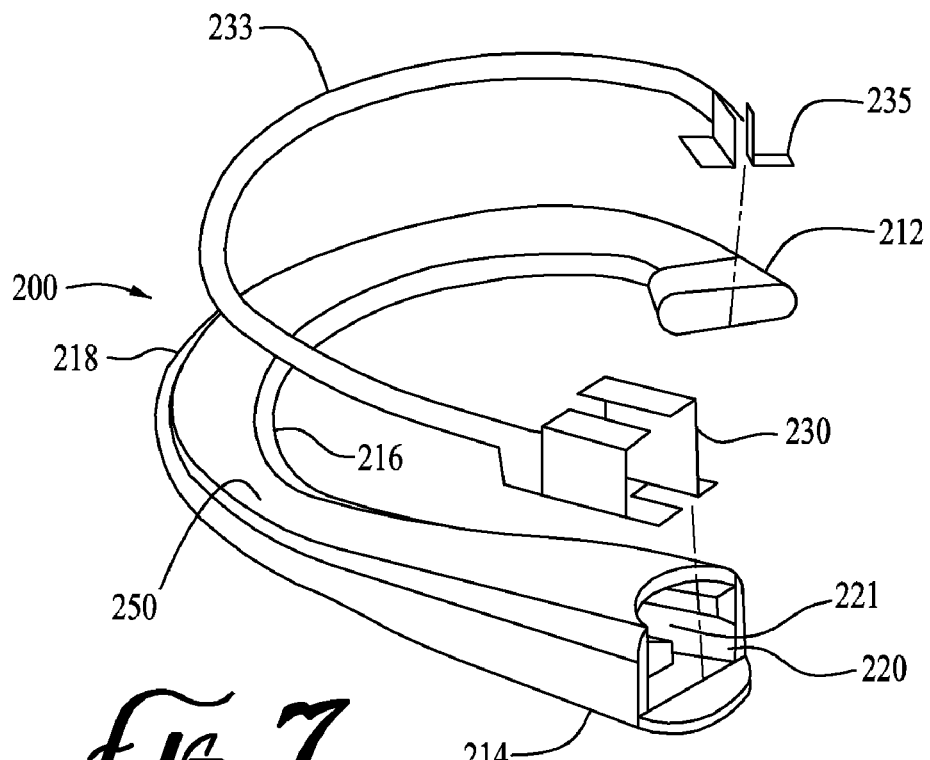
FIG. 7 is an exploded view of the ear hook of the device of FIG. 1.
Figure 9:
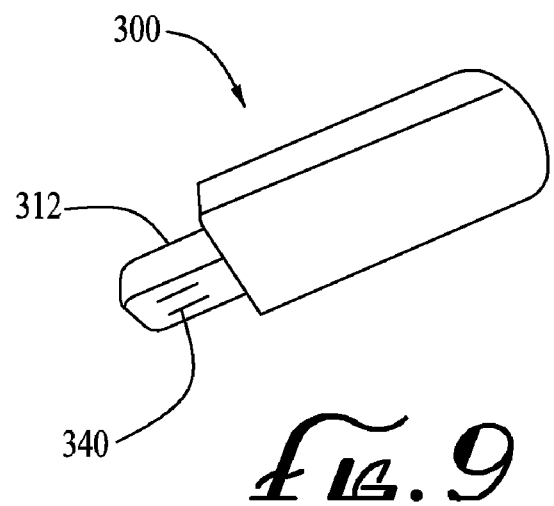
FIG. 9 is a lower perspective view of the battery housing shown in FIG. 8.

Preferably, the attachment between the housing 110 and the earhook 200 is a permanent attachment, i.e., it can not be reversed without damaging the housing 110 and or the earhook 200. The connection between the battery assembly 300 and the earhook 200, however, is preferably a reversible securable connection. As shown in FIG. 6, the battery assembly can be provided with a proximal end 312 which is configured to be inserted into an opening 220 at the distal end 214 of the earhook 200 and to be retained in the opening 220 via a friction fit. As best seen in FIG. 7, the opening 220 is provided in an interior portion 221 with a distal electrical contact 230 which is adapted to place the battery 330 into electrical communication with the electrical components of the earpiece 100. This is accomplished when electrical contacts 340 of the battery assembly 300 (seen in FIG. 9) are placed in electrical communication with the distal electrical contact 230, preferably through physical contact between these elements.

As shown in FIG. 7, the distal electrical contact 230 is in communication with a proximal electrical contact 235 at the proximal end 212 of the earhook 200 by means of an electrical connector 233 which extends between the electrical contacts 230 and 235. The electrical connector 233 can be a length of metal, as shown in FIG. 7, or can comprise a wire or other means of electrically connecting the electrical contacts 230 and 235.

One of the advantages of the present device 10 is that it is designed for comfort during sleep. One of the features providing such comfort in the embodiment of FIGS. 1-7 is the use of a substantially flat medial surface 240 and a substantially flat lateral surface 250 in the earhook 200. In this embodiment, the width of the earhook, that is the distance between the inner lateral extent 216 and outer lateral extent 218 of the earhook 200 is preferably at least two times, and preferably at least three times the distance between the medial surface 240 and the lateral surface 250 of the earhook along the majority of its longitudinal extent, and in particular at the proximal end 212 of the earhook 200. In this way, when a user wearing the present device 10 sleeps on his or her side, such that the ear carrying the present device 10 is pressed against a pillow, mattress, or other surface, the force exerted by the side of the user's head against the medial surface 240, and the force exerted by the lateral surface 250 against the medial side of the user's ear, will be spread across the substantially flat medial and lateral surfaces of the earhook 200. Spreading the force exerted against the user's head and ear in this way lessens the force exerted by the exterior of the present device 10 against any particular point of contact between the device and the user, thereby reducing discomfort. The medial surface 240 and lateral surface 250 also thus preferably do not include projections in areas that would contact a skin surface of a user.

Battery Assembly

The present device 10 is preferably powered by a source of stored energy so that no wired connection is necessary to power the transducer 150 and other electrical components of the present device 10. Preferably the power source is a battery 330, i.e. an electrochemical cell that can provide electrical power. In one embodiment the battery 330 can comprise one or more single-use batteries 330, in which case the battery housing 310 comprises a reversibly securable opening for retaining such batteries 330. In this context "reversibly securable" means that an opening can be changed from an open state to a closed state a plurality of times without compromising the mechanical structure of the battery housing 310. Preferably, however, the power source comprises one or more rechargeable batteries 330.

In embodiments in which the battery 330 is rechargeable, recharging can be accomplished in ways known to the art. For example, power from an external power source can be provided to the battery 330 through an electrical lead 340 extending from the power source to an electrical contact of the battery 330. The battery or batteries 330 can in this embodiment be rechargeable lithium ion, lithium ion polymer, nickel metal hydride, nickel-cadmium, or lead acid batteries, for example.

Figure 8:
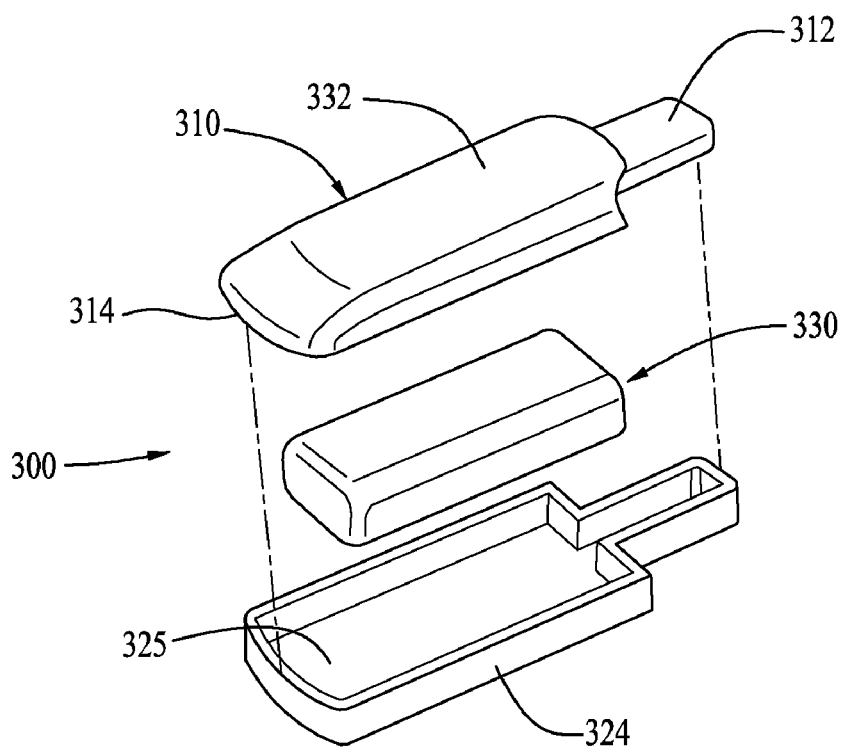
FIG. 8 is an exploded view of the battery assembly of the device of FIG. 1.

The battery 300 of the present device is preferably provided in a battery assembly 300 as shown in FIG. 8. In some embodiments, the battery assembly 300 can be fixedly attached to the earhook portion of the present device 200, such as by being integrally formed with the earhook 200, in which case the housing 310 of the battery assembly 300 would include a reversibly securable opening through which the battery 330 can be removed. In this case, the battery 330 can be either a single use battery or a rechargeable battery which is recharged through a separate recharging mechanism. Alternatively, the battery contained in an integrally formed or permanently secured earhook and battery assembly can be a rechargeable battery, and the battery assembly 300 can in this case be provided with circuitry for recharging the battery 330.

As shown in FIG. 8, in one embodiment, the battery assembly 300 can comprise a cover portion 322, a lower housing portion 320 and a lower hosing portion 324 having a compartment 325 for containing the battery 330. The battery assembly 300 is assembled by placing the battery 330 within the compartment 325 and then covering the battery with the battery cover 322. As with the earhook 200, the housing 310 of the battery assembly 300 preferably includes a substantially flat medial surface 340 and a substantially flat lateral surface 350 for providing comfort to a user during nighttime wear.

Transducer

A variety of types of transducers known to the art can be used in the present device. These include dynamic or moving coil types, which generally comprise a diaphragm connected to a central voice coil that moves within a magnetic field generated by a permanent magnet, and balanced armature types, which consist of a moving magnetic armature that is pivoted to move in the field of a permanent magnet. Other types of transducers can also be used, such as isodynamic, electrostatic, and electret type transducers.

MCU

Figure 12:
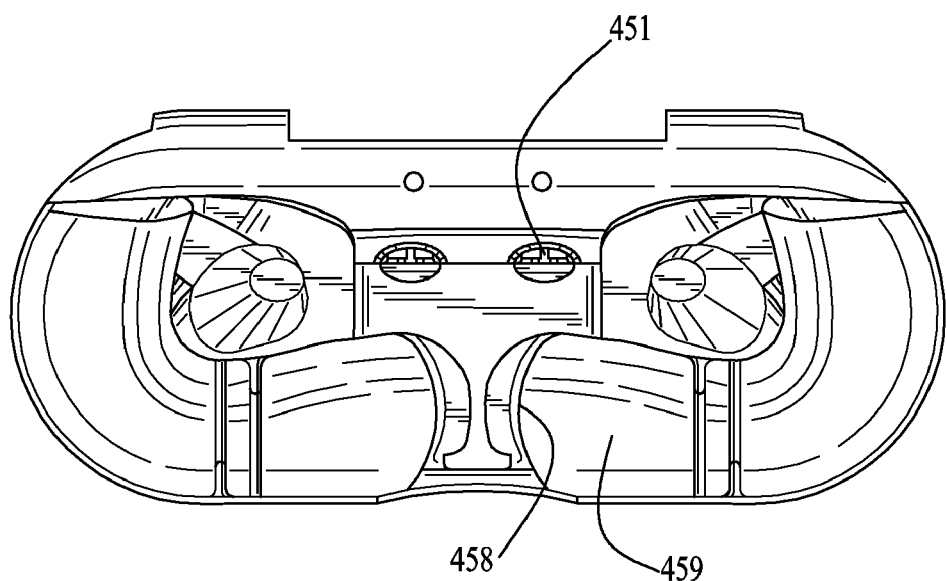
FIG. 12 is a top plan view of the lower portion of the storage case of FIG. 10.
Figure 13:
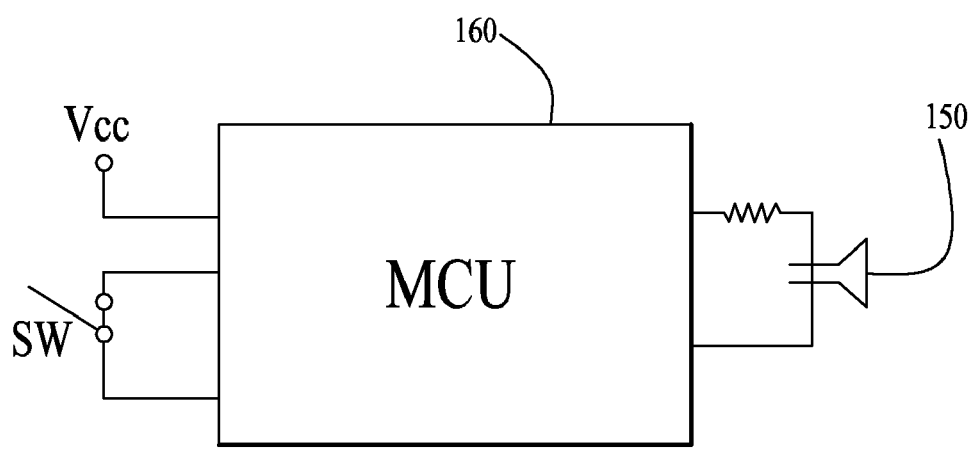
FIG. 13 is a circuit diagram of an MCU for use in the present device.

The MCU of the present device controls the generation of white noise, controls the volume of the white noise, and control the state of the device (on or off). FIG. 12 is a simplified circuit diagram of an embodiment of the present device showing an MCU 160 in electrical communication with other components of the present device. As shown in FIG. 12, the MCU 160 receives a source of common current (Vcc) and outputs a signal to the transducer 150. A switch (SW) in electrical communication with the MCU controls the on/off state of the device and volume. The MCU 160 is preferably located in the housing 110, but in alternative embodiments can be located within the battery assembly 300 and placed in electrical communication with the transducer 150.

Sound Generator

The sound generator in the present device preferably generates white noise, which can be produced in ways known to the art. Preferably, the white noise generator is a dedicated integrated circuit, which can be under the control of the MCU 160 of the present device 10. Alternatively, the MCU 160 can be programmed generate white noise. For example, an eight-pin Microchip PIC12C508 controller (available from Chandler, Ariz., USA) can be programmed to generate pseudorandom noise at its output pin. In a further alternative, the sound generator can comprise a noise cancellation circuit for generating an opposing-phase signal, in which case the present device further comprises a microphone for receiving external sounds, the microphone being in electrical communication with the noise cancellation circuit.

Storage Case

Figure 10:
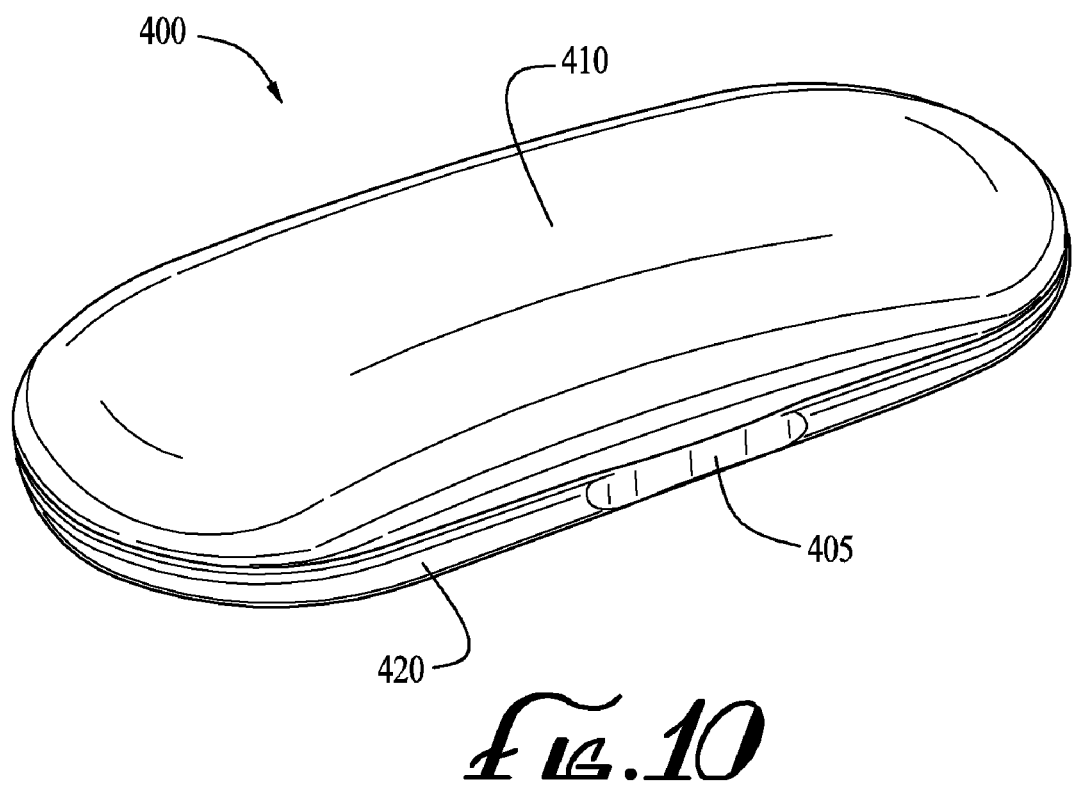
FIG. 10 is a perspective view of the exterior of a storage case for the present devices.
Figure 11:
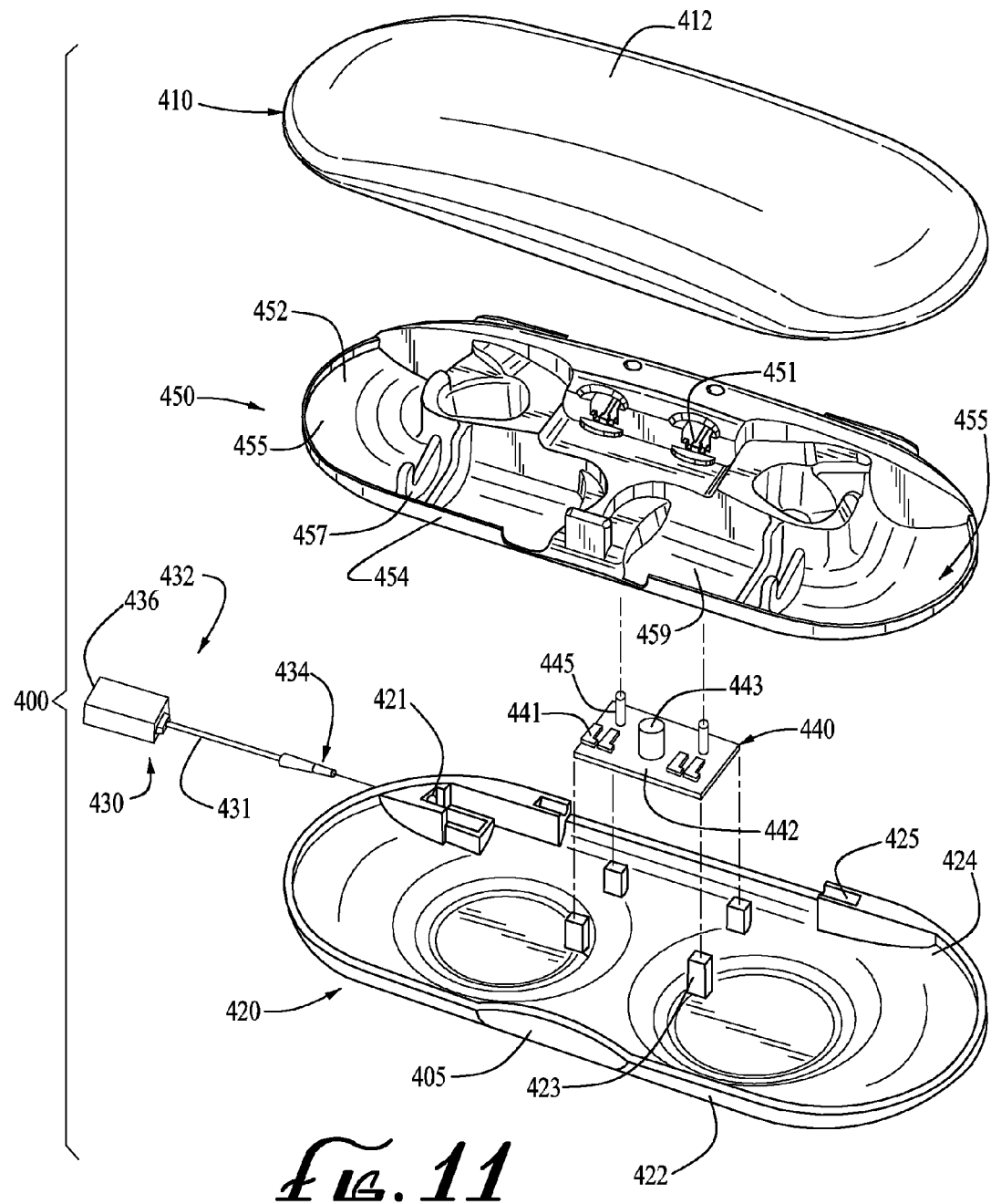
FIG. 11 is an exploded view of the storage case of FIG. 10.

In a preferred embodiment, the present device 10 is stored in a protective case 400, shown in FIGS. 10 and 11. The case 400 preferably comprises a base or receiving portion 420 for receiving the device 10 and a cover 410 having a protective upper surface 412 for covering the base 420 and protecting the device 10 when it is stored in the case 400. In the embodiment shown in FIGS. 10 and 11, the cover 410 and receiving portion 420 are hingedly connected in order to allow the case 400 to be reversibly opened and closed, though other means for opening and closing a covered container, such as through the use of snaps or other fasteners known to those of skill in the art, are also possible. In the embodiment shown in FIG. 11, the receiving portion 420 comprises barrel openings 425 for receiving corresponding pins attached to or integrally molded with the cover 410. The cover 410 and receiving portion 420 pivot about the hinge formed by the barrel 425 and the corresponding pin of the cover 410 in order to reversibly open and close the case 400. The cover 410 and receiving portion 420 can be reversibly secured in a closed state in ways known to the art, such as through the use of a clasp 405.

In order to protect the present device 10 from shock and damage when contained in the case 400, the case 400 and its structural components are preferably formed from a suitably rigid material, such as polypropylene. A compartment formed by concave portion 455 is also preferably provided in the case 400 for securely receiving and retaining the device 10. If needed, further supports 457 can be provided in the case 400 in order to prevent or limit the movement of the device 10 within the case 400.

In the embodiment shown in FIG. 11, the receiving portion 420 includes a formed insert 450. The insert 450 shown in this figure comprises two concave receiving portions 455 for receiving two of the present devices 10. Cases 400 which retain two of the present devices 10 are preferred since users of the present device in most cases are likely to use a device 10 in each ear in order to mask external sounds in both ears, such as during sleep.

Figure 14:
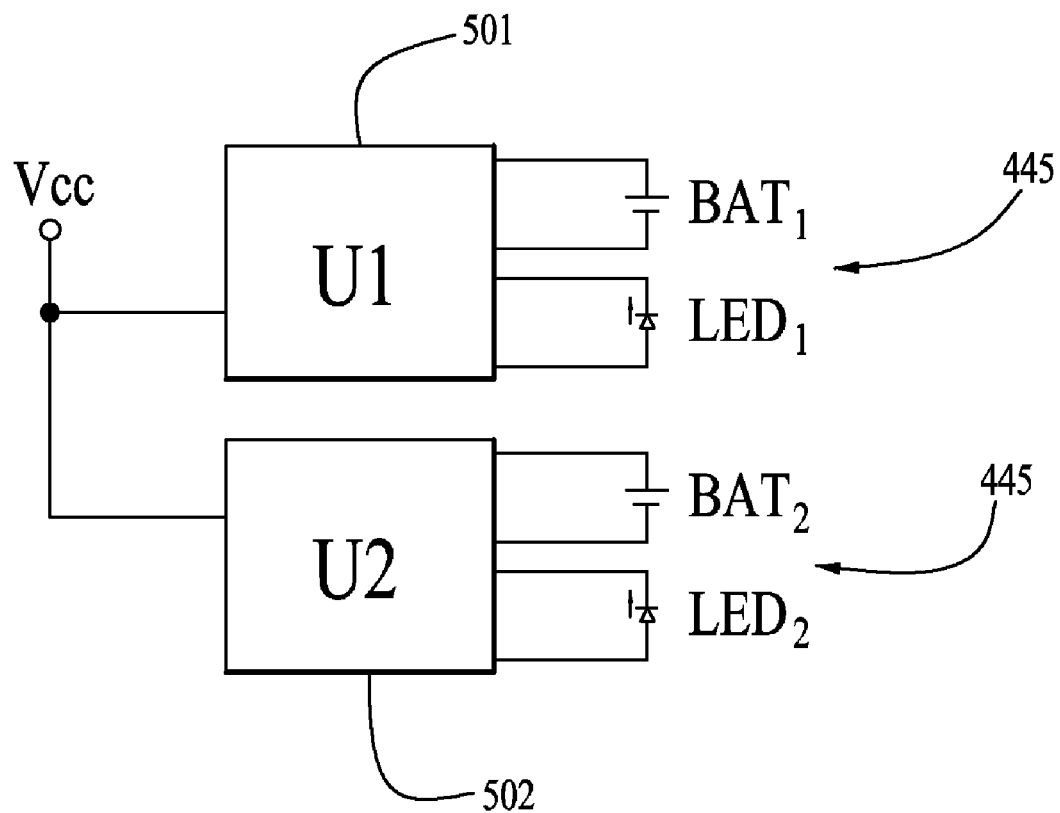
FIG. 14 is a circuit diagram for a battery charger that can be used in connection with the present device.

In a preferred embodiment, the present case 400 further comprises components needed to recharge the battery or batteries 330 of the present device 10. Such components include a circuit board 440, which in the embodiment shown in FIG. 11 is supported by posts 423 extending upwardly from and attached to the interior surface 424 of the receiving portion 420 of the case 400. The circuit board 440 retains and electrically connects further components of the battery charging assembly of the storage case 400. As shown in FIG. 14, this assembly includes a first integrated circuit 501 and a second integrated circuit 502 which can be placed in electrical communication with a source of common current using an electrical connector 430 (shown in FIG. 11). The circuit is placed in electrical communication with the electrical contacts 340 of the battery assembly 300 by means of circuit board contacts 441 retained on an upper surface 442 of the circuit board 440. The circuit shown in FIG. 14 further includes an LED 445 which in a preferred embodiment is a dual LED 445. When the battery 330 is in electrical communication with one of the circuits 501 or 502 and a source of common current, if the battery is not in a fully charged state, the LED 445 will produce a red light, but after reaching a voltage indicating a fully charged state, the circuit will cause the LED to produce a green light.

In order to place the battery assembly 300 in electrical communication with a source of common current, the circuit board contacts 441 are positioned in a receptacle 451 formed in the insert 450. The proximal end 312 of the battery assembly 300, which retains the electrical contacts 340, is configured to be received by and retained within the receptacle 451 when fully inserted into the receptacle 451. The electrical contacts 340 of the battery assembly 300 are also placed into physical contact with the electrical contacts 441 of the circuit board 440 when the insert 450 is positioned over the circuit board 440.

The circuit board 440 is electrically connected to a source of common current by means of an electrical connector 430 comprising a wire 431 having a distal end 434 adapted to be placed through an opening 421 in the receiving portion 420 of the present storage case 400 which is placed in electrical communication with the circuit board 440. A distal end 432 of the electrical connector 430 is then adapted to be placed in electrical communication with a source of current. In the embodiment of FIG. 11, the distal end 432 comprises a housing for a pin adapted to receive a corresponding female connector which can then place the electrical components of the storage case in communication with a source of common current, such as a transformer in communication with a source of alternating current.

The use of an insert 450 in the present storage case is not required. However, the use of such an insert is an advantage in manufacturing the present device, as the electronic components, including the circuit board 440 and electrical connector 430, can be retained between an interior surface 424 of the receiving portion 420 and a lower surface 454 of the insert 450. When suitably rigid materials are used to form both the receiving portion 420 and the insert 450, the foregoing electronic components of the storage case 400 are thereby protected from damage in view of being enclosed between the receiving portion 420 and the insert 450. In order to stabilize the circuit board 440 in such an embodiment, lower structural posts 423 and one or more upper structural posts 443 are provided below and above the circuit board 440, respectively.

A further advantage of the design shown in FIG. 11 is the orientation of the openings 451 with respect to a battery retaining portion 459 of the concave portion 455 of the insert 450. When the concave portion 455 of the insert 450 retains one of the present devices 10, the distal end 314 of the battery assembly 300 is adjacent to a distal end 458 of the concave portion 455. When the battery assembly 300 is removed from the earhook portion 200 of the present device and is inserted into the receptacle 451 for charging the battery, the distal end 314 of the battery assembly extends into the distal portion of the concave portion 455, i.e. the area 459 occupied by the battery assembly 300 when it is attached to the earhook, such that when the battery assembly 300 is inserted into the opening 451 it occupies some of the same space as when it is attached to the ear portion 200 and retained in the insert 450 of the storage case 400. In this way, the use of space within the storage case can be maximized and its overall size minimized.

Although the present invention has been described in considerable detail with reference to certain preferred embodiments, other embodiments are possible. The steps disclosed for the present methods, for example, are not intended to be limiting nor are they intended to indicate that each step is necessarily essential to the method, but instead are exemplary steps only. Therefore, the scope of the appended claims should not be limited to the description of preferred embodiments contained in this disclosure. All references cited herein are incorporated by reference in their entirety.

What is claimed is:

1. An aural device for reducing a user's experience of undesirable environmental noise, comprising:
   (a) a housing configured for placement adjacent to the ear canal of a user without covering the pinna, the housing having an interior, an exterior, a lateral end, and a medial end, comprising:
      (i) a transducer in the interior of the housing;
      (ii) circuitry in electrical communication with the transducer for generating sound, the circuitry comprising a white noise generator;
      (iii) a conduit for conducting sound generated by the transducer from the interior of the housing to the exterior of the housing, the conduit having a proximal end adjacent the transducer and a distal end adjacent the medial end of the housing; and
      (iv) an elastic rim adjacent to the distal end of the conduit for covering the ear canal of a user;
   (b) a projection having a proximal end connected to the housing, a distal end, a substantially flat lateral surface and a substantially flat medial surface, the projection comprising an electrical connector; and
   (c) a battery connected to the distal end of the electrical connector of the projection, wherein the battery is in electrical communication with the circuitry and the transducer through the electrical connector.

2. The device of claim 1, wherein the elastic rim comprises a distal surface which is spherical in shape.

3. The device of claim 1, wherein the elastic rim is an eartip.

4. The device of claim 1, wherein the projection comprises an earhook.

5. The device of claim 1, wherein the lateral end of the housing comprises a substantially flat surface.

6. The device of claim 5, wherein the medial end of the housing projects downward with respect to the substantially flat lateral end at an angle of less than 90°.

7. The device of claim 1, wherein the white noise generator generates noise selected from the group consisting of white noise, pink noise, blue noise, and black noise.

8. The device of claim 1, wherein the battery is contained in a battery housing having a proximal end, a distal end, a substantially flat lateral surface and a substantially flat medial surface.

9. The device of claim 8, wherein the proximal end of the battery housing is removably securable to the electrical connector.

10. The device of claim 9, wherein the battery is rechargeable.

11. A system comprising:
    (a) the aural device of claim 10; and
    (b) a container for the aural device, the container comprising:
        (i) a compartment retaining the aural device;
        (ii) a receptacle in the compartment for receiving the proximal end of the battery housing and placing the battery in electrical communication with a power source;
        (iii) circuitry for charging the battery.

12. The system of claim 11, wherein the container further comprises an LED light for indicating the charging status of the battery when it is contained in the receptacle.

13. The system of claim 11, wherein the container comprises an upper cover and a lower receiving portion, wherein the receiving portion further comprises a formed insert comprising the receptacle.

14. The system of claim 13, wherein the circuitry comprises a circuit board in the receiving portion for retaining and electrically connecting electrical components for charging the battery.

15. The system of claim 14, wherein the receiving portion comprises posts extending upwardly from a lower surface of the receiving portion for supporting the circuit board.

16. The system of claim 11, wherein the compartment retaining the aural device includes a distal portion for accommodating the battery housing when the battery housing is connected to the distal end of the projection of the aural device.

17. The system of claim 16, wherein when the proximal end of the battery housing is retained in the receptacle for charging the battery, the distal end of the battery housing extends into the distal portion of the compartment retaining the aural device.

* * * * *